United States Patent [19]

Krumkalns

[11] 4,039,675
[45] Aug. 2, 1977

[54] α,α-DIALKYL-SUBSTITUTED 3-PYRIDINEMETHANOLS AS FUNGICIDAL AGENTS

[75] Inventor: Eriks V. Krumkalns, Indianapolis, Ind.

[73] Assignee: Eli Lilly and Company, Indianapolis, Ind.

[21] Appl. No.: 351,675

[22] Filed: Apr. 16, 1973

Related U.S. Application Data

[63] Continuation-in-part of Ser. No. 289,530, Sept. 15, 1972, abandoned, which is a continuation-in-part of Ser. No. 14,223, Feb. 25, 1970, abandoned, which is a continuation-in-part of Ser. No. 609,000, Jan. 13, 1967, abandoned.

[51] Int. Cl.$^2$ .................... A01N 9/22; C07D 213/02
[52] U.S. Cl. ................................. 424/263; 260/297 R
[58] Field of Search .................... 424/263; 260/297 R

[56] References Cited

U.S. PATENT DOCUMENTS

| | | | |
|---|---|---|---|
| 2,727,895 | 12/1955 | Sperber et al. | 260/290 |
| 3,153,046 | 10/1964 | Hoffmann et al. | 260/293.4 |
| 3,203,855 | 8/1965 | Duerr et al. | 167/33 |
| 3,396,224 | 8/1968 | Van Heyningen | 424/263 |

OTHER PUBLICATIONS

Frear, Chem. of the Pesticides; p. 301.

*Primary Examiner*—Allen J. Robinson
*Attorney, Agent, or Firm*—Dwight E. Morrison; Everet F. Smith

[57] ABSTRACT

Fungi which attack agricultural crops and ornamental plants, are controlled by applying to the locus of the fungi α,α-dialkyl-substituted 3-pyridinemethanols or nonphytotoxic acid addition salts thereof.

4 Claims, No Drawings

α,α-DIALKYL-SUBSTITUTED 3-PYRIDINEMETHANOLS AS FUNGICIDAL AGENTS

CROSS-REFERENCE

This application is a continuation-in-part of my copending application, Ser. No. 289,530, filed Sept. 15, 1972 now abandoned, which was a continuation-in-part of my then copending application, Ser. No. 14,223, filed Feb. 25, 1970, now abandoned, which was a continuation-in-part of my then copending application Ser. No. 609,000, filed Jan. 13, 1967, now abandoned.

BACKGROUND OF THE INVENTION

Agricultural crops and ornamental plants are subject to attack by many kinds of fungi, both airborne and soilborne, with serious damage thereby resulting. A great amount of research has been conducted to find methods of combatting such fungi.

In the prior art, Sperber et al., U.S. Pat. No. 2,727,895 (Dec. 20, 1955), teach that certain 4-substituted pyridines, and the piperidines produced therefrom by hydrogenation of the pyridine ring, are useful primarily as anticonvulsants, and secondarily, as antibacterials and antifungals, when administered in a variety of the usual pharmaceutical forms, such as tablets, elixirs, solutions and capsules. Thus, the Sperber et al. compounds are directed toward use in animals or mammals. The claimed Sperber et al. compounds are α-phenyl-α-lower-alkyl-4-pyridylmethanes which thus differ significantly from the α,α-dialkyl-3-pyridine-methanols of the instant application. The Sperber et al. compounds showed minimal antifungal activity when compared with the dialkyl 3-pyridinemethanol compounds of the present application in tests against airborne and soil-borne fungi.

Another prior art reference is Hoffmann et al., U.S. Pat. No. 3,153,046 (October 13, 1964), which teaches dialkylpiperidylmethanols as having fungicidal, and especially antibacterial, properties useful against *Microsporum audouini*, *Trichophyton interdigitalis*, and *Staphylococcus aureus*, and against tubercle bacilli. Hoffmann et al. teach that their compounds can be used as disinfectants, preservatives, or as medicaments for the treatment of bacterial infections, and thus the compounds are implicitly directed to use in humans or animals. Such piperidyl compounds, which are produced by hydrogenating the intermediate pyridine compounds, for which pyridine compounds no activity is taught, have shown minimal activity in tests against plant pathogenic fungi.

Duerr et al., U.S. Pat. No. 3,203,855 (Aug. 31, 1965), teach a method for combatting phytopathogenic organisms, i.e., fungi or bacteria, using the compound 2-(2,2,2-trichloro-1-hydroxyethylamino)pyridine, which compound differs significantly from those described in the instant application.

Also in the prior art is Van Heyningen, U.S. Pat. No. 3,396,224 (Aug. 6, 1968), which teaches that substituted 3-pyridylmethane derivatives are active against phytopathogenic fungi. Optimum fungicidal activity was disclosed by Van Heyningen for his compounds only when both substituents were aryl. Thus, compounds disclosed by Van Heyningen showed optimum activity against airborne fungi and little or no activity against soil-borne fungi. This is in contrast to the instant dialkyl 3-pyridinemethanol compounds which most unexpectedly show their optimum activity against soil-borne fungi.

It is believed that a unique method of controlling fungi using α,α-dialkyl-substituted 3-pyridinemethanols has been found.

SUMMARY

This invention relates to novel methods and compositions for the control of both airborne and soil-borne fungi which attack plants. More particularly, this invention concerns novel methods and compositions for controlling such fungi using α,α-dialkyl-substituted 3-pyridinemethanols or the nonphytotoxic acid addition salts thereof.

DESCRIPTION

The novel methods and compositions of the present invention have been found useful in controlling airborne and soil-borne fungi which attack agricultural crops and ornamental plants.

Among the susceptible fungi which attack agricultural crops are *Erysiphe polygoni*, the causative organism of bean powdery mildew; and *Uromyces phaseoli* var. Typica, the causative organism of bean rust.

In addition, the novel compositions containing one or more of the α,α-dialkyl-substituted 3-pyridinemethanols coming within the scope of the above formula are effective against *Rhizoctonia solani*, the soil-borne organism causing damping-off of cucumbers and of cotton; against *Pythium aphanidermatum*, the causative agent of damping-off of cotton; and against *Verticillium albo-atrum*, the causative organism of verticillium wilt of tomato.

It is an object of the present invention to provide novel methods and compositions for controlling the growth of airborne and soil-borne fungi which are pathogenic to agricultural crops and to ornamental plants. It is a further important object of the invention to provide compositions which are toxic to such fungi.

In fulfillment of the above and other objects, this invention provides a novel process which comprises applying to the locus of the fungi a fungicidal amount of one or more substituted 3-pyridinemethanols of the class represented by the formula:

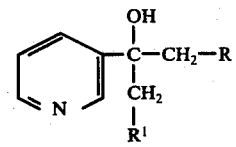

wherein

R and $R^1$ are the same or different, and are $C_3$–$C_{16}$ alkyl or $C_3$–$C_8$ cycloalkyl; or an acid addition salt thereof.

$C_3$–$C_{16}$ Alkyl means saturated aliphatic hydrocarbon radicals, both straight-chain and branched-chain, having from three to sixteen carbon atoms in the chain, and can be illustratively n-propyl, isopropyl, n-butyl, sec.-butyl, isobutyl, t-butyl, n-amyl, sec.-amyl, isoamyl, tert.-amyl, n-hexyl, sec.-hexyl, isohexyl, tert.-hexyl, n-heptyl, isoheptyl, sec.-heptyl, n-octyl, isooctyl, sec.-octyl, n-nonyl, sec.-nonyl, isononyl, n-decyl, sec.-decyl, isodecyl, n-dodecyl, sec.-dodecyl, hendecyl, tridecyl, tetradecyl, pentadecyl, hexadecyl, and the like.

$C_3$–$C_8$ Cycloalkyl means saturated monocyclic aliphatic hydrocarbon radicals having three to eight carbons in the ring and includes cyclopropyl, cyclobutyl, cyclopentyl, cyclohexyl, cycloheptyl, and cyclooctyl. It is to be understood that these $C_3$-$C_8$ cycloaliphatic radicals may be optionally substituted with halogen, or methyl, ethyl, propyl, isopropyl, n-butyl, isobutyl, secondary butyl, or t-butyl radicals.

Suitable salts of the bases represented by the above formula can be prepared employing for example the following acids: hydrochloric, hydrobromic, sulfuric, phosphoric, nitric, oxalic, methanesulfonic, p-toluenesulfonic, maleic, and the like. It will be understood by those skilled in the art that suitable salts include those which are not substantially more phytotoxic than the free bases from which they are derived.

Compounds coming with the scope of the generic formula, supra, include, but are not limited to, the following:

α,α-Bis(n-pentyl)-3-pyridinemethanol
α,α-Bis(isopentyl)-3-pyridinemethanol hydrochloride
α-n-Amyl-α-n-hexyl-3-pyridinemethanol
α,α-Bis(n-undecyl)-3-pyridinemethanol
α-n-Hexyl-α-n-heptyl-3-pyridinemethanol
α,α-Bis(cyclohexylmethyl)-3-pyridinemethanol hydrochloride
α-Isopentyl-α-isohexyl-3-pyridinemethanol hydrobromide
α,α-Bis(n-hexyl)-3-pyridinemethanol hydrochloride
α-n-Undecyl-α-n-nonyl-3-pyridinemethanol sulfate
α,α-Bis(isopentyl)-3-pyridinemethanol hydrobromide
α-n-Dodecyl-α-n-octyl-3-pyridinemethanol phosphate
α,α-Bis(n-hexyl)-3-pyridinemethanol sulfate
α,α-Bis(n-undecyl-3-yridinemethanol phosphate
α,α-Bis(sec.-nonyl)-3-pyridinemethanol oxalate
α,α-Bis(n-dodecyl)-3-pyridinemethanol hydrochloride
α,α-Bis(hendecyl)-3-pyridinemethanol hydrochloride
α,α-Bis(cycloheptylmethyl)-3-pyridinemethanol
α,α-Bis(cyclopropylmethyl)-3l -pyridinemethanol
α,α-Bis(cyclobutylmethyl)-3-pyridinemethanol
α,α-Bis(cyclooctylmethyl)-3-pyridinemethanol
α,α-Bis(cyclopentylmethyl)-3-pyridinemethanol
α,α-Bis(n-octyl)-3-pyridinemethanol hydrobromide, and the like.

The compounds useful in the novel fungicidal process of this invention can be synthesized by a preparative method taught by Wibaut et al., Rec. Trav. Chim., 77, 1057 (1958). According to the Wibaut et al. method, 3-pyridyllithium, prepared by the reaction of butyllithium with 3-bromo- or 3-iodopyridine in ether, is allowed to react in a nitrogen atmosphere with a suitable dialkyl ketone in ether solution at a temperature of about −50° to −60° C. to yield an α,α-dialkyl-substituted 3-pyridinemethanol. The procedure can be suitably illustrated by the following description of the preparation of α,α-bis(isopentyl)-3-pyridinemethanol.

To 400 ml. of anhydrous ethyl ether contained in a 1-liter, 3-neck, round-bottom flask, equipped with a mechanical stirrer, and cooled in an acetone-Dry Ice bath, was added 54 g. (0.13 mole) of a 15 percent solution of n-butyllithium in n-hexane. Nitrogen gas was continuously introduced into the reaction flask to prevent air oxidation of the n-butyllithium. When the temperature of the solution had fallen to −70° C., a solution of 16 g. (0.1 mole) of 3-bromopyridine in 100 ml. of anhydrous ethyl ether was added dropwise while maintaining the reaction mixture temperature below −50° C. The reaction was allowed to proceed for about 45 minutes at −60° C. to assure complete conversion of the 3-bromopyridine to 3-pyridyllithium. A solution of 17 g. (0.1 mole) of diisopentyl ketone in 100 ml. of anhydrous ethyl ether was added dropwise while maintaining the reaction mixture temperature at −50° to −60° C. during the addition. The reaction product mixture was stirred for about 2 hours at about −60° C., and then allowed to warm to room temperature overnight.

The excess butyllithium was decomposed by the addition of 100 ml. of cold water to the reaction product mixture. The organic layer was separated and dried over anhydrous sodium sulfate overnight. The dry ether solution was filtered off, concentrated in vacuo, and distilled to yield α,α-bis(isopentyl)-3-pyridinemethanol as an oil having a boiling point of about 134° C. at 0.1 mm. The product was identified by infrared and n.m.r. spectra and by elemental analysis.

The nonphytotoxic acid addition salts are readily prepared by methods well known to the art. The free base is dissolved in ether, the solution cooled and saturated with, for example, anhydrous hydrogen chloride gas. The hydrochloric acid addition salt of the substituted 3-pyridine-methanol which precipitates is filtered off and purified by recrystallization from a suitable solvent.

In carrying out the method of the present invention, compositions containing the active ingredient are applied to the locus of the fungi, e.g., infected or susceptible plant surfaces, or the soil. In the case of the soil, the application is allowed to remain as a coating on the surface of the soil, or alternatively, incorporated into the soil by disking, hoeing, or other methods well known to those skilled in the art. A convenient and preferred method of application is to spray the plant or soil surfaces with a liquid dispersion or emulsion of the active ingredient. The fungicidally-active α,α-dialkyl 3-pyridinemethanol compounds have also been found to be effective when incorporated in a seed coat applied to seeds prior to planting.

The compositions of the present invention desirably contain, in addition to the substituted 3-pyridinemethanol antifungal, one or more of a plurality of additaments including water, polyhydroxy compounds, petroleum distillates, and other dispersion media, surface-active dispersing agents, emulsifiers, and finely-divided inert solids. The concentration of the substituted pyridine antifungal in these compositions may vary depending on whether the compositon is intended for direct application as a dust to plants or is intended as an emulsifiable concentrate of a wettable powder designed to be subsequently diluted with additional inert carrier such as water to produce the ultimate treating composition.

The compounds of the present invention are applied in effective amounts, varying somewhat with the severity of the fungus infection and with other factors such as the environment in which treatment is conducted. In general, it will be found that an aqueous apray containing from about 16 to about 400 ppm. of active material is satisfactory when the application to plants is to be carried out in the greenhouse.

As is well understood in the art, a somewhat higher concentration of the fungicide is desirable when treatment of the plants is to be carried out in the field. In that case, the preferred range is from about 80 to about 600 ppm. of the 3-substituted pyridinemethanol compound. Thus, it can be seen that the range of desirable concentration of the fungicide in an aqeuous spray ranges from about 16 to about 600 ppm., depending upon whether the spray is to be applied to plants in the greenhouse or in the field.

In the case of the soil pathogens, supra, control has been accomplished using a broadcast application rate of from about 5 to 40 lb. per acre of the 3-substituted pyridine-methanol compound.

When the substituted 3-pyridinemethanol is applied in a seed coating, satisfactory control has been accomplished when the seed coating contains from about 100 to about 2000 ppm. of the fungicidal pyridinemethanol compound.

Treating compositions are most conveniently formulated by preparing liquid or solid concentrates, which are subsequently diluted to the desired level for use. Emulsifiable liquid concentrates can be prepared by incorporating from about 1 to about 10 percent by weight of the active ingredient and an emulsifying agent in a suitable water-immiscible organic liquid. Such concentrates may be further diluted with water to form spray mixtures in the form of oil-in-water emulsions. Such spray compositions then comprise active toxicant, water-immiscible solvent, emulsifying agent, and water. Suitable emulsifying agents can be of the nonionic or ionic types, or blends thereof, and include condensation products of alkylene oxides with phenols and organic acids, polyoxyethylene derivatives of sorbitan esters, complex ether-alcohols, ionics of the aralkyl sulfonate type, and the like. Suitable water-immiscible organic liquids to be employed include aromatic hydrocarbons, aliphatic hydrocarbons, cycloaliphatic hydrocarbons, and mixtures thereof such as petroleum distillates.

Solid concentrate mixtures can be prepared by incorporating from about 10 to about 50 percent by weight of the substituted pyridinemethanol compound in a finely-divided solid carrier such as bentonite, fuller's earth, diatomaceous earth, hydrated silica, diatomaceous silica, expanded mica, talc, chalk, and the like. Such concentrates can be formulated, if desired, for direct use as dusting compositions, or can be diluted, if desired, with additional inert solid carriers to produce dusting powders containing around 0.05 to 1 percent by weight of the substituted 3-pyridinemethanol. Alternatively, surfactants, that is, dispersing and/or wetting agents, can be incorporated along with the substituted pyridinemethanol in the solid carrier to form wettable powder concentrates ranging from about 10 to about 25 percent by weight concentration which subsequently can be dispersed in water or other hydroxylated carrier to form spray compositions. Suitable surfactants include condensed aryl sulfonic acids and sodium salts thereof, sodium lignosulfate, sulfonate-oxide condensate blends, alkyl aryl polyether alcohols, sulfonate/-nonionic blends, anionic wetting agents, and the like.

Further, the substituted pyridine toxicant can be incorporated in solutions, simple dispersions, aerosol formulations, and other media adaptable to be employed for treating vegetation or applying to the soil.

In operating according to the method of the present invention, the antifungal composition is applied to infected or susceptible plant surfaces in any convenient fashion such as spraying, dusting, dipping, or drenching. A spray method is considered preferable, especially when large numbers of plants are involved, because of the rapidity and uniformity of treatment possible. In spraying, it is usually sufficient for the infected or susceptible surfaces to be thoroughly wet with the liquid dispersion employed. Good results have been obtained by employing spray compositions whether they be emulsions or aqueous dispersions of solid concentrates.

Where the fungi to be controlled are in the soil, the antifungal compounds can be applied to the soil directly or they can be diluted with various inert solid or liquid diluents, as described above, and then applied to the fungusinfested area. The preferred level of broadcast application for control of soil-inhabiting fungi is from about 5 to about 40 pounds per acre as set forth, supra. For an in-furrow application in the field, an application rate of from about 0.5 to about 4 lb./acre is used. Thus, for the control of soil-inhabiting fungi, the application rate varies from about 0.5 to about 40 pounds per acre, depending on the method of application. When an acid addition salt of a dialkyl 3-pyridinemethanol base is used, the rate of application will, of course, depend on the amount of base actually present, since the acids which form salts with these pyridines contribute little or nothing to the fungicidal activity of the base, and the salts themselves are employed chiefly for ease of handling and formulating.

Where a fungicidal pyridine compound coming within the scope of the generic formula, supra, is applied in a seed coating, a coating formulation is prepared containing a suitable dye, together with other excipients such as glycerin, hydroxypropyl methyl cellulose, isopropyl alcohol, acetone, methylene chloride, and the like. The dye, for example, F.D. and C. Red No. 2, is merely added to identify the seeds as being coated and treated. The seeds are mixed in a miniature coating pan using a mixture of the coating formulation and a solution of the desired pyridine fungicide.

More specifically, the use of the $\alpha,\alpha$-dialkylsubstituted 3-pyridinemethanols represented by the above formula, and acid addition salts thereof, can be illustrated by the following procedures.

EXAMPLE 1

The evaluation of the effectiveness of compounds exemplified by the above formula against *Erysiphe polygoni*, the causative organism of bean powdery mildew, was accomplished in the greenhouse in the following manner.

Fungicidal compositions were prepared by dissolving 40 mg. of the compound to be tested in 1 ml. of a solution of cyclohexanone containing 55 mg. of sulfonate/-nonionic blend and diluting to a volume of 100 ml. with water. This composition then contained 400 ppm. of fungicide.

Three bean seeds (Kentucky Wonder variety) were planted in 4-inch clay pots and allowed to germinate. The plants were thinned to two plants per pot. Ten days after the day of planting the seeds, the test chemicals, compounded as described above, were sprayed on all leaf surfaces of the bean plants and allowed to dry. The plants were then placed in the greenhouse and Kentucky Wonder beans heavily infested with powdery mildew were placed above them until the end of the test period. Twenty days after planting, the plants were observed for development of the disease. The appearance of the treated plants was compared with that of untreated plants and ratings of the control of the fungus (protection rating) were recorded. The protection rating scale used was as follows:

1 — no control
2 — slight control
3 — moderate control

4 — good control
5 — complete control, no fungus

Chart 1, which follows, sets forth the results of the testing of several substituted 3-pyridinemethanols against *Erysiphe polygoni*. Chart 2 sets forth the results of testing several 2-pyridine and 4-pyridinemethanols taught by Sperber et al., U.S. Pat. No. 2,727,895 (Dec. 20, 1955). Chart 3 sets forth the results of testing several 3-piperidinemethanols taught by Hoffmann et al., U.S. Pat. No. 3,153,046 (Oct. 13, 1964). In all charts, Column 1 gives the name of the compound; Column 2, the rate in terms of ppm. at which the compound was applied to the test plants; and Column 3, the protection rating of the compound.

Chart 1

| Compound | Appln. Rate ppm. | Protection Rating |
| --- | --- | --- |
| α,α-Bis(n-butyl)-3-pyridinemethanol hydrochloride | 400<br>80<br>16 | 3.5<br>2<br>3 |
| α,α-Bis(isopentyl)-3-pyridinemethanol hydrochloride | 400<br>80<br>16<br>3.2 | 4−<br>2.5<br>2<br>3 |
| α,α-Bis(n-undecyl)-3-pyridinemethanol | 400<br>80<br>16 | 4.5<br>3<br>2 |
| α,α-Bis(n-hexyl)-3-pyridinemethanol hydrochloride | 400<br>80<br>16<br>3.2 | 4<br>4+<br>2.5<br>2 |
| α,α-Bis(cyclohexyl-methyl)-3-pyridine-methanol hydrochloride | 400<br>80<br>16 | 4.5<br>4<br>1.5 |
| α,α-Bis(n-pentyl)-3-pyridinemethanol | 400<br>80<br>16 | 5<br>5<br>4+ |
| α-(n-Hexyl)-α-isobutyl-3-pyridinemethanol | 400 | 3− |
| α,α-Bis(isobutyl)-3-pyridinemethanol | 400 | 3 |

Chart 2

| Compound | Appln. Rate ppm. | Protection Rating |
| --- | --- | --- |
| α,αBis(n-hexyl)-2-pyridinemethanol | 400 | 1 |
| α,α-Bis(n-pentyl)-2-pyridinemethanol | 400 | 1 |
| α,α-Bis(n-propyl)-4-pyridinemethanol | 400 | 2 |

Chart 3

| Compound | Appln. Rate | Protection Rating |
| --- | --- | --- |
| α,α-Bis(n-hexyl)-3-piperidinemethanol | 400 | 1 |
| α,α-Bis(cyclohexyl-methyl)-3-piperidine-methanol | 400 | 1 |
| α,α-Bis(isopentyl)-3-piperidinemethanol | 400 | 1 |
| α,α-Bis(isobutyl)-3-piperidinemethanol | 400 | 1 |
| α,α-Bis(n-butyl)-3-piperidinemethanol | 400 | 1 |
| α,α-Bis(n-pentyl)-3-piperidinemethanol | 400<br>80<br>16 | 1<br>1<br>1 |
| Control | 0 | 1 |

EXAMPLE 2

The following experimental procedure was used to demonstrate the efficacy of certain compositions of this invention to inhibit the growth of *Uromyces phaseoli* var. typica, the causative organism of bean rust.

Bean plants were grown from seeds planted in sand contained in 4-inch plastic pots, three bean seeds of the Pinto variety being planted in each pot.

On the tenth day after planting the seeds, the bean plants were infected by spraying the foliage with a spore suspension of *Uromyces phaseoli* var. typica.

The compound to be tested was weighed out and dissolved in a mixture of aqueous 1 percent cyclohexanone as a solvent and aqueous 0.1 percent polyoxyethylene sorbitan monolaurate as a surfactant to give a concentration of test compound of 400 ppm. A 5-ml. portion of this solution was placed in a test tube and diluted to a volume of 50 ml. with aqueous 0.085 percent sodium chloride solution to give a concentration of test compound of 40 ppm., the concentration at which the present test was carried out. The sodium chloride solution was used to provide an isotonic medium for the plants. A bean plant was removed from the sand in a pot, the roots washed with water and the plant placed in a test tube containing a solution of the compound being tested. The plants in the test tubes were placed in the greenhouse for a period of 10 days. During this time, the roots of each plant were aerated for about 10 to 15 minutes four times daily, air being introduced into the bottom of the test tube via a capillary tube. At the end of 10 days, the plants were examined for evidence of the development of bean rust and compared with two plants which had been inoculated with *Uromyces phaseoli* var. typica and placed in test tubes containing all ingredients except the test chemicals.

Chart 4, which follows, sets forth the results of testing the dialkyl 3-pyridinemethanols against *Uromyces phaseoli* var. typica. Chart 5 sets forth the results of testing several dialkyl 2-pyridine and 4-pyridinemethanols against the same organism. Chart 6 sets forth the results of testing several dialkyl 3-piperidinemethanols against the same organism. The protection rating scale used was the same as for Example 1.

Chart 4

| Compound | Appln. Rate ppm. | Protection Rating |
| --- | --- | --- |
| α,α-Bis(isopentyl)-3-pyridinemethanol hydrochloride | 40 | 5 |
| α,α-Bis(n-butyl)-3-pyridinemethanol hydrochloride | 40 | 4+ |
| α-(n-Heptyl)-α-isobutyl-3-pyridinemethanol | 40 | 3 |
| α-(n-Hexyl)-α-isobutyl-3-pyridinemethanol | 40 | 3− |
| α,α-Bis(isobutyl)-3-pyridinemethanol | 40 | 5 |
| α,α-Bis(n-pentyl)-3-pyridinemethanol | 40 | 3 |

Chart 5

| Compound | Appln. Rate ppm. | Protection Rating |
| --- | --- | --- |
| α,α-Bis(n-hexyl)-2-pyridinemethanol | 40 | 1 |
| α,α-Bis(n-pentyl)-2-pyridinemethanol | 40 | 1 |
| α,α-Bis(n-propyl)-4-pyridinemethanol | 40 | 1 |

Chart 6

| Compound | Appln. Rate ppm. | Protection Rating |
| --- | --- | --- |
| α,α-Bis(n-hexyl)-3-piperidinemethanol | 40 | 1 |
| α,α-Bis(cyclohexyl- | 40 | 1 |

Chart 6-continued

| Compound | Appln. Rate ppm. | Protection Rating |
|---|---|---|
| methyl)-3-piperidine-methanol | | |
| $\alpha,\alpha$-Bis(isopentyl)-3-piperidinemethanol | 40 | 1 |
| $\alpha,\alpha$-Bis(isobutyl)-3-piperidinemethanol | 40 | 1 |
| $\alpha,\alpha$-Bis(n-butyl)-3-piperidinemethanol | 40 | 1 |
| $\alpha,\alpha$-Bis(n-pentyl)-3-piperidinemethanol | 40 | —* |
| Control | 0 | 1 |

*Killed the plants

EXAMPLE 3

The evaluation of the effectiveness of compounds exemplified by the above formula against *Rhizoctonia solani*, the causative organism of damping-off of cucumbers, was accomplished in the greenhouse in the following manner.

A concentrated solution of each compound to be tested was prepared by first dissolving the compound in 2 milliliters of 50 percent (by volume) acetone-ethyl alcohol solution and then bringing the solution up to the desired volume by diluting with aqueous 0.1 percent polyoxyethylene sorbitan monolaurate solution. In those cases where the compound was insoluble in the acetone-ethyl alcohol solvent, the mixture was transferred to a tissue grinder and micropulverized to yield a suspension.

One hundred twenty-five grams of silty sand infested with *Rhizoctonia solani* from turf, was placed in a No. 60 canfreeze jar. in an indentation made in the surface of the silty sand was placed 3 grams of 30–60 mesh granulated diatomaceous earth. The diatomaceous earth was then impregnated with four (4) milliliters of test solution prepared as described above, this being equivalent to an application rate of 40 lb./acre. Impregnation of the diatomaceous earth with 2 milliliters of test solution is equivalent to an application rate of 20 lb./acre. The can-freeze jar was first hand shaken for a few seconds and then placed on a roller for several minutes to thoroughly incorporate the test compound in the silty sand. A portion of the treated-infested silty sand was transferred to a 2.5 inch plastic pot and planted with 12 cucumber seeds (Green Prolific variety). The seeds were covered with the remaining silty sand to a depth of one-half inch. All the pots were then placed in a temperature-humidity controlled growth cubicle in the greenhouse and watered as needed. After 14 days, the cucumber seedlings were examined, compared with the check plants, and the results recorded. The protection rating scale used was the same as for the previous examples. The results are set forth in Chart 7 for the testing of the dialkyl 3-pyridinemethanols against *Rhizoctonia solani*. Chart 8 sets forth the results of testing several dialkyl 3-piperidinemethanols against the same organism.

Chart 7

| Compound | Appln. Rate lb./acre | Protection Rating |
|---|---|---|
| $\alpha,\alpha$-Bis(isobutyl)-3-pyridinemethanol | 40 | 5 |
| | 20 | 5 |
| | 10 | 5 |
| | 5 | 4 |
| $\alpha,\alpha$-Bis(cyclohexyl-methyl)-3-pyridine-methanol | 40 | 4.3 |
| | 20 | 4.3 |
| | 10 | 5 |
| $\alpha$-(n-Hexyl)-$\alpha$-isobutyl- | 40 | 4 |

Chart 7-continued

| Compound | Appln. Rate lb./acre | Protection Rating |
|---|---|---|
| pyridinemethanol hydrochloride | | |
| $\alpha,\alpha$-Bis(n-butyl)-3-pyridinemethanol hydrochloride | 40 | 3.3 |
| $\alpha$-(n-Heptyl)-$\alpha$-isobutyl-3-pyridinemethanol | 40 | 4.6 |
| | 20 | 4.3 |
| | 10 | 3 |
| $\alpha,\alpha$-Bis(n-pentyl)-3-pyridinemethanol | 40 | 5 |
| | 20 | 5 |
| | 10 | 5 |
| | 5 | 4 |
| $\alpha,\alpha$-Bis(n-butyl)-3-pyridinemethanol | 40 | 5 |
| | 20 | 5 |
| | 10 | 4 |
| $\alpha,\alpha$-Bis(cyclohexyl-methyl)-3-pyridine-methanol hydrochloride | 40 | 5 |
| | 20 | 3 |
| | 10 | 1 |
| $\alpha,\alpha$-Bis(n-hexyl)-3-pyridinemethanol hydrochloride | 40 | 3 |
| | 20 | 1 |
| | 10 | 1 |

Chart 8

| Compound | Appln. Rate lb./acre | Protection Rating |
|---|---|---|
| $\alpha,\alpha$-Bis(n-pentyl)-3-piperidinemethanol | 40 | 1 |
| | 20 | 1 |
| | 10 | 1 |
| $\alpha,\alpha$-Bis(n-hexyl)-3-piperidinemethanol | 40 | 1 |
| | 20 | 1 |
| | 10 | 1 |
| $\alpha,\alpha$-Bis(isopentyl)-3-piperidinemethanol | 40 | 1 |
| | 20 | 1 |
| | 10 | 1 |
| $\alpha,\alpha$-Bis(isobutyl)-3-piperidinemethanol | 40 | 1 |
| | 20 | 1 |
| | 10 | 1 |
| $\alpha,\alpha$-Bis(n-butyl)-3-piperidinemethanol | 40 | 1 |
| | 20 | 1 |
| | 10 | 1 |

EXAMPLE 4

The evaluation of the effectiveness of compounds exemplified by the above formula against *Rhizoctonia solani*, the causative organism of damping-off of cotton, was accomplished in the greenhouse in the following manner.

A bench containing Rhizoctonia-inoculated soil is maintained in the greenhouse as a source of simulated field soil for this test. This source of infested soil is kept virulent through periodic reinoculations with Rhizoctonia-infested wheat seed whenever the bench is replenished with ordinary greenhouse soil. To maintain the pathogenicity of the organism, cotton (Coker 100 A variety) is heavily seeded in the soil to provide host plants. When used, the soil is screened to remove organic debris and then diluted with an equal volume of unsterile greenhouse soil.

The test compound, 14.2 mg., equivalent to a broadcast application rate of 40 lb./acre, was dissolved in 0.5 ml. of 50 percent by volume of acetone-ethyl alcohol solvent, and the volume brought up to 5 ml. with aqueous 0.1 percent polyoxyethylene sorbitan monolaurate. To the solution thus obtained was added 3 gm. of 30–60 mesh granulated diatomaceous earth to act as a carrier. One hundred fifty grams of fungus-infested soil was added to the jar, the jar capped and rolled on a roller for 3 minutes to thoroughly incorporate the test chemical in the soil.

The treated, infested soil was then transferred to a 3-inch square pot, planted to 10 cotton seeds, variety Coker 100 A, and placed on a cart in the greenhouse.

After about 7 to 9 days, the seedling plants were examined and the results read and recorded, using the same rating scale as for the previously described tests. Results are recorded in Chart 9, which follows.

Chart 9

| Compound | Appln. Rate lb./acre | Protection Rating |
|---|---|---|
| α-(n-Heptyl)-α-isobutyl-3-pyridinemethanol | 40 | 3.5 |
| | 20 | 3 |
| | 10 | 4 |
| | 5 | 4 |
| α,α-Bis(n-pentyl)-3-pyridinemethanol | 40 | 5 |
| | 20 | 5 |
| | 10 | 5 |
| | 5 | 5 |
| α-(3-Ethyl-n-pentyl)-α-isobutyl-3-pyridinemethanol hydrochloride | 40 | 4 |
| | 20 | 3.5 |
| | 10 | 3.5 |
| | 5 | 4 |
| α-(n-Hexyl)-α-isobutyl-3-pyridinemethanol hydrochloride | 40 | 3.5 |
| | 20 | 3 |
| | 10 | 3 |
| | 5 | 3 |
| α,α-Bis(n-butyl)-3-pyridinemethanol | 40 | 4 |
| | 20 | 2.5 |
| | 10 | 2.5 |
| | 5 | 3 |
| α,α-Bis(isobutyl)-3-pyridinemethanol | 40 | 4 |
| | 20 | 4.5 |
| | 10 | 4 |
| | 5 | 1 |

EXAMPLE 5

A field trial was run to determine the efficacy of α,α-bis(cyclohexylmethyl)-3-pyridinemethanol hydrochloride against *Rhizoctonia solani*, the causative organism of damping-off of cotton.

A wettable powder formulation of the pyridine fungicide was prepared by mixing the following ingredients: 22.5 parts of α,α-bis(cyclohexylmethyl)-3-pyridinemethanol hydrochloride; 4.5 parts of a dispersing agent, the neutral sodium salt of condensed aryl sulfonic acid; 9.1 parts of a nonionic surfactant, an alkyl aryl polyether alcohol; 1.8 parts of precipitated hydrated silicon dioxide; 4.5 parts of an anionic surfactant, sodium N-methyl-N-palmitoyl taurate; and 57.6 parts of kaolin clay. The wettable powder thus formulated contained approximately 23 percent of the fungicidally-active, dialkyl 3-pyridinemethanol. The wettable powder, in 10 gal. of water, was applied in the furrow at planting time, using a carbon dioxide pressurized sprayer at a pressure of 30 lb. Cotton (*Cossypium hirsutum*), variety Coker 413, was the test plant.

The testing was carried out using a randomized complete block design, with 3 replicates per test. The rows were spaced 40 inches apart, in sandy soil having an organic content of 1.0 to 2.0 percent as shown by testing. Fertilizer (6-6-6) was applied at the rate of 1000 lb. per acre after bedding, and the blocks were sprinkler-irrigated with ¾ inch of water after planting to assure germination of the cotton seeds. Each plot was inoculated with *Rhizoctonia solani*-infested oats at the rate of 1.5 lb. per 100 sq. feet.

The efficacy of the test compound was determined by counting the number of cotton plants which emerged per 10 feet of row in the plots. The counting was done on the 4th, 5th, 6th, 7th, 8th, and 17th day after planting. Five untreated checks of 3 replicates each were also run. The results are recorded in Chart 10, and are the average of the 3 replicates of each run.

Chart 10

| Compound | lb./acre | No. of plants emerged/10 ft. of row | | | | | |
|---|---|---|---|---|---|---|---|
| | | 4–19 | 4–20 | 4–21 | 4–22 | 4–23 | 5–2 |
| α,α-Bis(cyclohexyl-methyl)-3-pyridine-methanol hydrochloride | 0.5 | 6.0 | 9.7 | 12.0 | 11.7 | 13.3 | 5.7 |
| | 1.0 | 4.3 | 11.0 | 13.7 | 13.3 | 15.3 | 7.3 |
| | 2.0 | 3.3 | 10.0 | 14.3 | 17.3 | 17.7 | 13.7 |
| Untreated checks | 0 | 1.8 | 4.8 | 6.5 | 6.9 | 6.5 | 1.3 |

EXAMPLE 6

The efficacy of one of the compounds α,α-bis(cyclohexylemthyl)-3-pyridinemethanol hydrochloride, against *Rhizoctonia solani*, the causative agent of damping-off of cucumber and damping-off of cotton, when applied as a seed overcoat, was determined in the greenhouse.

A coating formulation was prepared containing the following quantities of ingredients per 100 ml. of formula: 0.005 g. F.D. and C. Red No. 2; 0.376 g. of glycerin; 3.000 g. hydroxypropyl methyl cellulouse −50; 45.000 ml. isopropyl alcohol, N.F.; 5.000 ml. acetone; with mixing and dilution to a volume of 100 ml. with methylene chloride.

Seventy-five grams of cucumber seeds (Green Prolific variety) was mixed in a miniature coating pan using a mixture of 0.75 g. of the above-described coating formulation, and 0.15 ml. of a methanol solution containing 50 mg. of α,α-bis-(cyclohexylmethyl)-3-pyridinemethanol hydrochloride per milliliter. Using these ingredients in these amounts produced a seed coating containing 100 ppm. of the fungicidal compound.

For a seed coating containing 1000 ppm. of the fungicidal compound, 1.50 ml. of a methanol solution containing 50 mg./ml. of α,α-bis(cyclohexylmethyl)-3-pyridinemethanol hydrochloride was mixed in the miniature coating pan with 75 g. of cucumber seeds (Green Prolific variety), together with 0.75 g. of the previously described coating formulation.

And for a seed coating containing 2000 ppm. of the fungicidal compound, 3.00 ml. of a methanol solution containing 50 mg./ml. of α,α-bis(cyclohexylmethyl)-3-pyridinemethanol hydrochloride was mixed in the miniature coating pan with 75 g. of cucumber seeds (Green Prolific variety), together with 0.75 g. of the previously described coating formulation. The seeds were then planted.

In a similar fashion, seeds of cotton, Stoneville variety, were coated with α,α-bis(cyclohexylmethyl)-3-pyridinemethanol hydrochloride, and the seeds planted.

In both the cucumber and cotton tests, three replicates were run at each concentration of fungicide in the seed overcoat. The results are listed in Chart 11 which follows. The protection ratings are the same as used in Examples 1–4 above:

Chart 11

| Compound | Dosage | Plant | Protection Rating |
|---|---|---|---|
| α,α-bis(cyclohexyl-methyl)-3-pyridine-methanol hydrochloride | 2000 ppm. | Cucumber | 3.3 |
| | 1000 ppm. | Cucumber | 3.6 |
| | 100 ppm. | Cucumber | 2.3 |
| Blank overcoat | 0 ppm. | Cucumber | 1.3 |
| α,α-bis(cyclohexyl-methyl)-3-pyridine- | 2000 ppm. | Cotton | 4.3 |
| | 1000 ppm. | Cotton | 3.3 |

Chart 11-continued

| Compound | Dosage | Plant | Protection Rating |
|---|---|---|---|
| methanol hydrochloride | 100 ppm. | Cotton | 4.6 |
| Blank overcoat | 0 ppm. | Cotton | 1.0 |

EXAMPLE 7 the evaluation of the effectiveness of compounds exemplified by the above formula against *Pythium aphanidermatum*, the causative organism of Pythium damping-off of cotton, was accomplished in the greenhouse in the following manner.

Enough sterilized soil to fill twenty 4-inch pots was thoroughly mixed with 100 ml. of fungus-infested wheat seed of the test organism. The fungi were allowed to grow through the soil for several days and then the mixture was processed through a screen to remove the organic debris and diluted with an equal volume of sterile soil.

A broadcast rate equivalent to 40 lb./acre (14.2 mg.) of the test compound was weighed out and placed in a jar, dissolved in 0.5 ml. of 50 percent (by volume) of acetone-ethyl alcohol solution, and then the solution brought up to the desired volume of 5 ml. by the addition of aqueous 0.1 percent polyoxyethylene sorbitan monolaurate solution. To the solution thus obtained was added 3 g. of 30–60 mesh granulated diatomaceous earth to serve as a carrier.

To the above mixture in the jar was added 150 g. of Pythium-infested soil and the jar and contents rolled for three minutes to thoroughly incorporate the test chemical in the soil. The treated, infested soil was then immediately transferred to a 3-inch square pot, planted to 10 cotton seeds, variety Coker 100 A, and placed on a greenhouse cart. The pots on the cart were then covered with a polyethylene cover and the cart placed in a temperature-humidity controlled growth cubicle in the greenhouse. After 72 hours, the polyethylene cover was removed and the cotton seedlings allowed to grow. In about 7 to 9 days after planting the seeds, the cotton seedlings were examined, compared with the check plants, and the results recorded. The protection rating scale was used the same as for the previous examples. Results are set forth in Chart 12.

Chart 12

| Compound | Appln. Rate lb./acre | Protection Rating |
|---|---|---|
| α-(n-Heptyl)-α-isobutyl-3-pyridinemethanol | 40 | 3 |
| α,α-Bis(n-pentyl)-3-pyridinemethanol | 40 | 4 |
| | 20 | 4 |
| | 10 | 4 |
| | 5 | 3 |
| α-(3-Ethyl-n-pentyl)-α-isobutyl-3-pyridinemethanol hydrochloride | 40 | 3 |
| α-(n-Hexyl)-α-isobutyl-3-pyridinemethanol hydrochloride | 40 | 2 |
| | 20 | 3 |
| | 10 | 3 |
| | 5 | 3 |
| α,α-Bis(n-butyl)-3-pyridinemethanol | 40 | 4 |
| | 20 | 3.5 |
| | 10 | 3 |

EXAMPLE 8

The evaluation of the effectiveness of compounds exemplified by the above formula against *Verticillium albo-atrum*, the causative organism of Verticillium wilt of tomatoes, was accomplished in the greenhouse in the following manner.

Enough sterilized soil to fill twenty 4-inch pots was thoroughly mixed with 50 ml. of wheat seed which had been heavily infested with a strain of the test organism tht specifically incites wilt of tomato plants. The fungus was allowed to grow through the soil for several days. The soil was then processed through a screen to remove the organic debris, and diluted with an equal volume of sterile soil.

Fourteen and two-tenths milligrams of test compound, which is equivalent to a broadcast treatment rate of 40 lb./acre, was weighed out and placed in a No. 60 can-freeze jar. The test compound was dissolved in 0.5 ml. of 50 percent by volume of an acetone-ethyl alcohol solution. The volume was then brought up to 5 ml. by the addition of aqueous 0.1 percent polyoxyethylene sorbitan monolaurate solution, and 3 gm. of 30–60 mesh granulated diatomaceous earth was added to the solution to act as a carrier. One hundred fifty g. of infested soil was added to the jar, the jar cap screwed in place, and the jar contents were rolled for 3 minutes to thoroughly incorporate the test chemical in the soil. After the mixing was complete, the jar caps were loosened to a very loose fit to allow the volatile chemical fumes to escape. The jars were then placed in a humidity-temperature controlled growth cubicle in the greenhouse for 5 days.

At the end of 5 days, the contents of each of the jars were transferred to 3-inch square pots, and a tomato plant, variety Bonny Best, about 4–5 inches tall, was transplanted into the soil of each pot as an indicator plant. Results were recorded when the leaves of the infested check plants were wilted 75 percent. The protection rating scale used was the same as for the previous examples. Results are set forth in Chart 13.

Chart 13

| Compound | Appln. Rate lb./acre | Protection Rating |
|---|---|---|
| α-(3-Ethyl-n-pentyl)-α-isobutyl-3-pyridinemethanol hydrochloride | 40 | 4 |
| | 20 | 4 |
| | 10 | 4 |
| α,α-Bis(n-pentyl)-3-pyridinemethanol | 40 | 5 |
| | 20 | 5 |
| | 10 | 3 |
| α-(n-Heptyl)-α-isobutyl-3-pyridinemethanol | 40 | 3 |
| α,α-Bis(n-hexyl)-3-pyridinemethanol hydrochloride | 40 | 5 |

I claim:

1. A method for controlling plant pathogenic fungi which comprises applying to the locus of the fungi a fungicidally-effective amount of α,α-bis(n-pentyl)-3-pyridinemethanol.

2. A method for controlling plant pathogenic fungi which comprises applying to the locus of the fungi a fungicidially-effective amount of α,α-bis(isopentyl)-3-pyridinemethanol hydrochloride.

3. A method for controlling plant pathogenic fungi which comprises applying to the locus of the fungi a fungicidally-effective amount of α,α-bis(n-hexyl)-3-pyridinemethanol hydrochloride.

4. A composition for controlling plant pathogenic fungi comprising a fungicidally-effective amount of α,α-bis(n-pentyl)-3-pyridinemethanol, an inert solid diluent and a surfactant.

* * * * *

UNITED STATES PATENT OFFICE
CERTIFICATE OF CORRECTION

Patent No. 4,039,675           Dated August 2, 1977

Inventor(s) Eriks V. Krumkalns

It is certified that error appears in the above-identified patent and that said Letters Patent are hereby corrected as shown below:

Column 3, line 33:  "3-yridinemethanol" should read --3-pyridinemethanol--.

Column 3, line 39:  "31-" should read --3---.

Column 4, line 57:  "apray" should read --spray--.

Column 6, line 7:   "fungusinfested" should read --fungus-infested--.

Column 9, line 34:  "canfreeze jar. in" should read --can-freeze jar. In--.

Column 11, line 54: "Cossypium" should read --Gossypium--.

Column 12, line 17: "clohexylemthyl" should read --clohexylmethyl--.

Column 13, line 9:  "the" should read --The--.

Column 14, line 6:  "tht" should read --that--.

Signed and Sealed this

Fourteenth Day of February 1978

[SEAL]

Attest:

RUTH C. MASON
Attesting Officer

LUTRELLE F. PARKER
Acting Commissioner of Patents and Trademarks